US008156795B2

(12) United States Patent
Batchelder et al.

(10) Patent No.: US 8,156,795 B2
(45) Date of Patent: Apr. 17, 2012

(54) SYSTEM AND METHOD FOR MEASURING SURFACE ENERGIES

(76) Inventors: John Samuel Batchelder, Somers, NY (US); Cynthia T. Batchelder, Somers, NY (US)

( * ) Notice: Subject to any disclaimer, the term of this patent is extended or adjusted under 35 U.S.C. 154(b) by 442 days.

(21) Appl. No.: 12/445,826

(22) PCT Filed: Oct. 23, 2006

(86) PCT No.: PCT/US2006/041327
§ 371 (c)(1),
(2), (4) Date: Apr. 16, 2009

(87) PCT Pub. No.: WO2008/051214
PCT Pub. Date: May 2, 2008

(65) Prior Publication Data
US 2010/0206057 A1    Aug. 19, 2010

(51) Int. Cl.
*G01B 5/28* (2006.01)
(52) U.S. Cl. .......................................................... 73/105
(58) Field of Classification Search ...................... 73/105
See application file for complete search history.

(56) References Cited

U.S. PATENT DOCUMENTS

| 5,163,317 A | 11/1992 | Ono et al. |
| 5,311,767 A * | 5/1994 | Mathews et al. ................. 73/843 |

OTHER PUBLICATIONS

International Search Report and Written Opinion of Counterpart Application No. PCT/US2006/41327 Filed on Oct. 23, 2006.

* cited by examiner

*Primary Examiner* — Lisa Caputo
*Assistant Examiner* — Octavia Davis-Hollington
(74) *Attorney, Agent, or Firm* — Brian R. Morrison; Westman, Champlin & Kelly, P.A.

(57) ABSTRACT

An apparatus (402) and method for measuring a surface energy of a test surface (12), which includes a viscoelastic polymer layer (20), disposed on a moveable component (34), that is compressed against the test surface (12) with a compressive force. The moveable component (34) is then moved relative to the test surface (12) at a predetermined velocity, and a drive force applied to the moveable component (34) is measured. The surface energy of the test surface (12) is then determined based at least in part on the compressive force, the predetermined velocity, and the measured drive force.

20 Claims, 11 Drawing Sheets

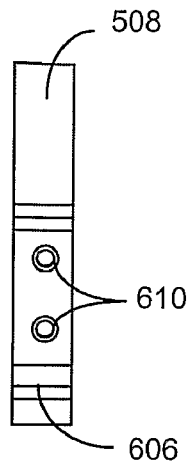 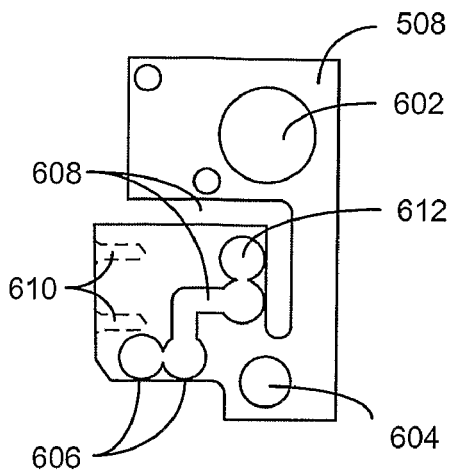
FIG 6A.    FIG 6B.
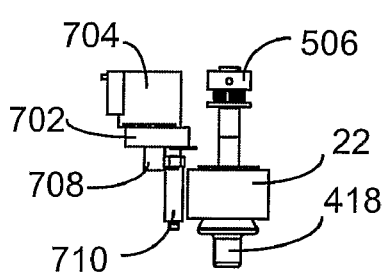 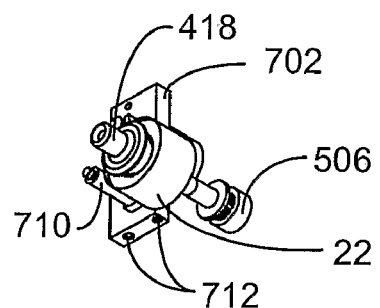
FIG 7A.    FIG 7B.
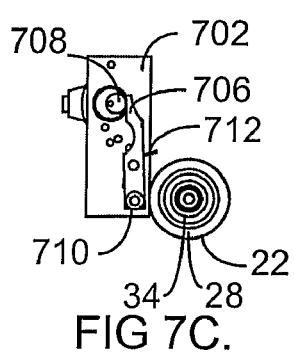 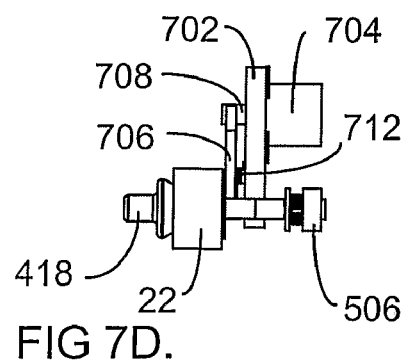
FIG 7C.    FIG 7D.

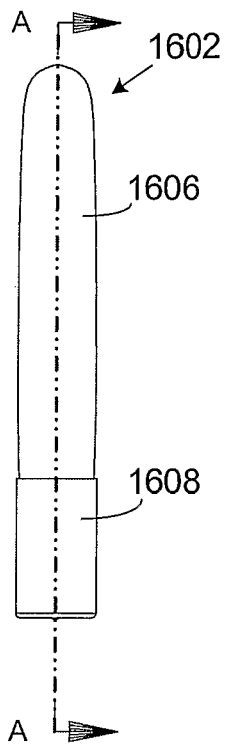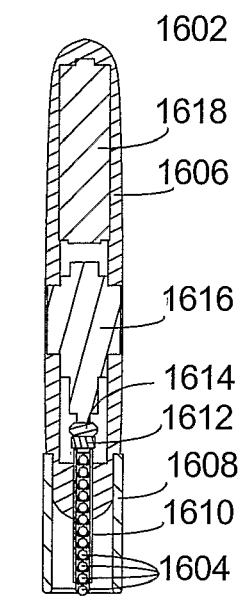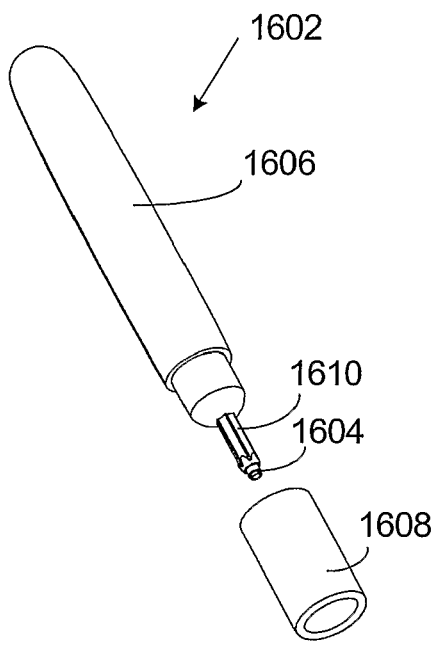
FIG 16A.  FIG 16B.  FIG 16C.
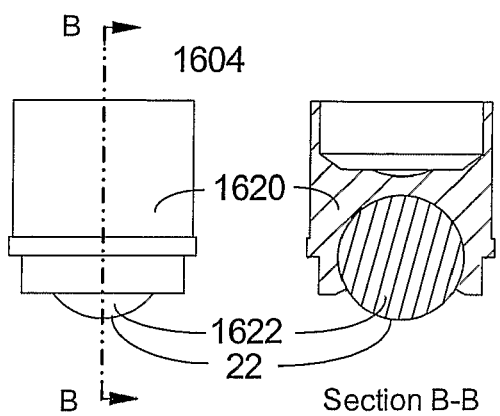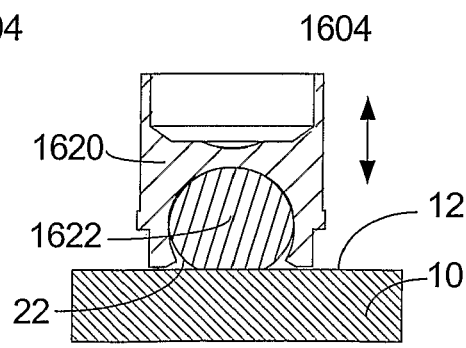
FIG 16D.  FIG 16E.  FIG 16F.

SYSTEM AND METHOD FOR MEASURING SURFACE ENERGIES

FIELD OF THE INVENTION

This invention relates to an apparatus and a method for measuring the surface energy of a test surface to assess its ability to be bonded. The invention finds particular use in manufacturing control systems to verify the preparation of surfaces to be bonded.

BACKGROUND OF THE INVENTION

Mechanisms that contribute to adhesion at the interface between two solids include polar and non-polar dispersion, hydrogen bonding, covalent and metallic bonding, charged bilayers, cross-linking, polymer entanglement, and mechanical locking. Many manufacturing bonding processes rely on these mechanisms, including painting, printing, plating, adhering, soldering, and spinning. Measurements of surface energy are often used to assess if a surface has been suitably prepared for bonding.

The surface free energy of a solid is typically defined as half the energy per unit area required to separate a solid into two half planes separated by vacuum. U.S. Pat. No. 5,477,732 describes bringing a characterized solid atomic force microprobe (AFM) into intimate contact with a surface under test, and then measuring the energy required to separate the probe and test surface. The high curvature of the probe tip makes the technique insensitive to most roughness of the test surface. Small AFM tips are generally formed from relatively hard, high surface energy materials.

Attempting a similar touch probe between a probe and test surface on a more convenient larger scale encounters the problem that most solid surfaces are somewhat rough and unclean. Most of the above mentioned forces are very short range, so that roughness that separates the two surfaces by a few Angstroms on average will reduce the measured force of attraction by more than an order of magnitude.

While small scale roughness of the surface to be adhered is generally an impediment to measuring the surface energy of that surface, it often improves bonding of the manufactured article. The standard approach to probe rough surfaces is to use a liquid that wets the rough surface to some degree. The surface tension of a liquid is the analog of the surface free energy of a solid. In particular, measuring the contact angle of a sessile droplet on the test surface has been related to the surface free energy of the test surface using relations like the Young-Dupre equation. Related liquid contact angle measurements include the Wilhelmy plate method, the fiber contact angle method, the pendant drop method, and the Du Nouy ring method. Applying droplets of different composition increase the range of measurable surface energies, and allow some differentiation between component contributions from dispersion, polar, and hydrogen bonding.

Surface roughness remains a problem for contact angle measurements. This is observed in several ways. Since the slope of the test surface is not constant along wetting line around a sessile drop, the wetting line can be a scalloped circle instead of a smooth circle. Typically the drying contact angle is smaller than the wetting contact angle, in part because surface roughness can generate a hysteresis that tends to pin the wetting line. The microscopic contact angle at the wetting front can be different from the measurable macroscopic contact angle.

BRIEF SUMMARY OF THE INVENTION

The present invention relates to an apparatus and method for measuring a surface energy of a test surface having a plurality of asperities and pits, where a viscoelastic polymer layer, disposed on a moveable component, is positioned in contact with the test surface and compressed with a compressive force. The moveable component is then moved relative to the test surface at a predetermined velocity, and a drive force applied to the moveable component is measured. The surface energy of the test surface is then determined based at least in part on the compressive force, the predetermined velocity, and the measured drive force.

One object of this invention is to improve the above compliant solid probe to account for variations in the observed force resulting from changes in the test surface roughness.

Another object of this invention is to provide a convenient, inexpensive, and portable meter for rapidly assessing the adequate preparation of surfaces to be bonded.

Another object of this invention is to improve the range of surface energies that can be probed compared to those accessible to contact angle measurement techniques.

Another object of this invention is to provide a self-calibration technique for verifying the veracity of the probe surface.

Another object of this invention is to provide a method to test the relative adhesion of the test surface to a probe surface composed of a polymeric material selected to be most similar to the intended bonding material.

Another object of this invention is to provide information on the spatial variation of the surface energy of the test surface.

Another object of this invention is to increase the reusability of the compliant solid probe by using non-overlapping sectors of its surface for independent measurements.

Another object of this invention is to provide protection for the compliant solid probe so that it is not contaminated while not in use.

BRIEF DESCRIPTION OF THE DRAWINGS

FIGS. 6A and 6B illustrate side and front views, respectively, of the torque measurement flexure of a preferred embodiment of the invention.

FIG. 7A is a top view of the portable, battery operated meter, showing features associated with a self-calibration mechanism.

FIG. 7B is a bottom perspective view of the portable, battery operated meter, showing features associated with the self-calibration mechanism.

FIG. 7C is a side view of the portable, battery operated meter, showing features associated with the self-calibration mechanism.

FIG. 7D is a front view of the portable, battery operated meter, showing features associated with the self-calibration mechanism.

FIG. 16A is a side view of a complete apparatus, which is a preferred embodiment of the invention in a compact configuration.

FIG. 16B is a sectional view of section A-A taken in FIG. 16A.

FIG. 16C is a perspective view of the complete apparatus with a standoff separated.

FIG. 16D is a side view of a disposable applicator assembly.

FIG. 16E is a sectional view of section B-B taken in FIG. 16D.

FIG. 16F is also a sectional view of section B-B taken in FIG. 16D.

DETAILED DESCRIPTION

As a viscoelastic material is peeled off of a surface, work is expended both in fracturing the interface (the surface energy) and in distorting the viscoelastic material (mechanical dissipation). Typically the work expended in mechanical dissipation is much greater than the work needed to overcome the surface energy. For example, the surface energy of polystyrene is about 0.033 Joules per square meter. Conceptually, if a one-atom-thick film could be peeled off of the surface, so that no energy is expended distorting the film, the force required to pull away a one centimeter wide film would be about 330 micro Newtons for polystyrene (independent of the rate that it is peeled). Peeling a typical removable pressure sensitive adhesive (PSA) strip one centimeter wide from polystyrene will typically require several Newtons, or more than 100 times the energy required to overcome the surface energy, and the required force varies considerably with the rate that the strip is peeled. Viscoelastic dissipation therefore acts as a desirable amplifier of the interfacial surface energy, making a small force easier to measure.

Figure 1A:
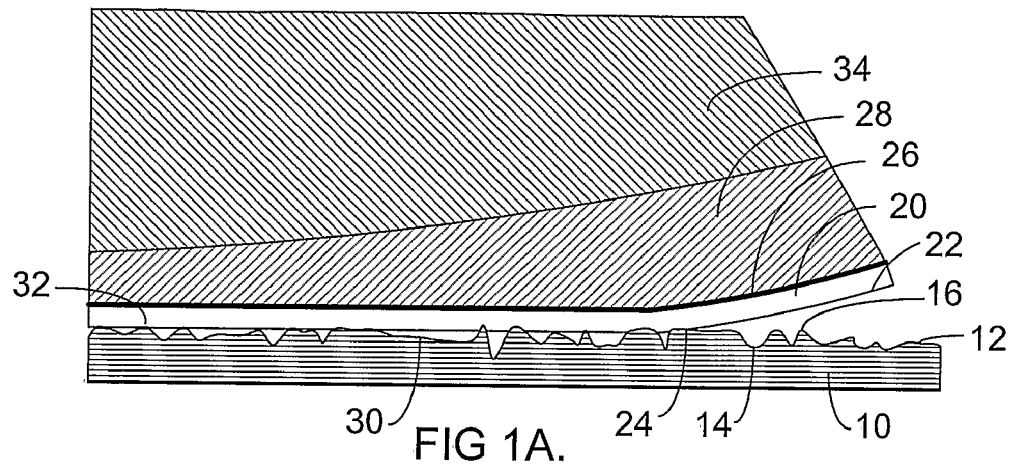
FIG. 1A is a sectional view illustrating a method of applying a viscoelastic probe surface to a test surface.
Figure 1B:
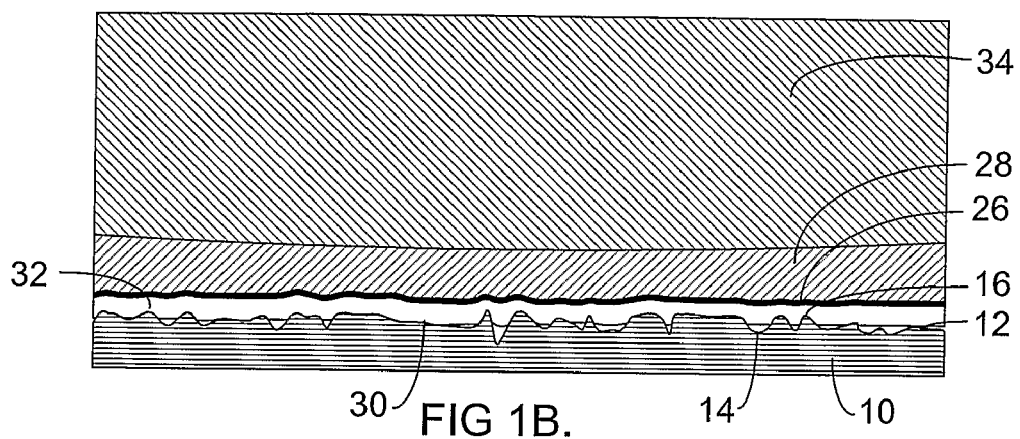
FIG. 1B is a sectional view illustrating a method of applying creep and relaxation to obtain an intimate contact between the probe and test surface.
Figure 1C:
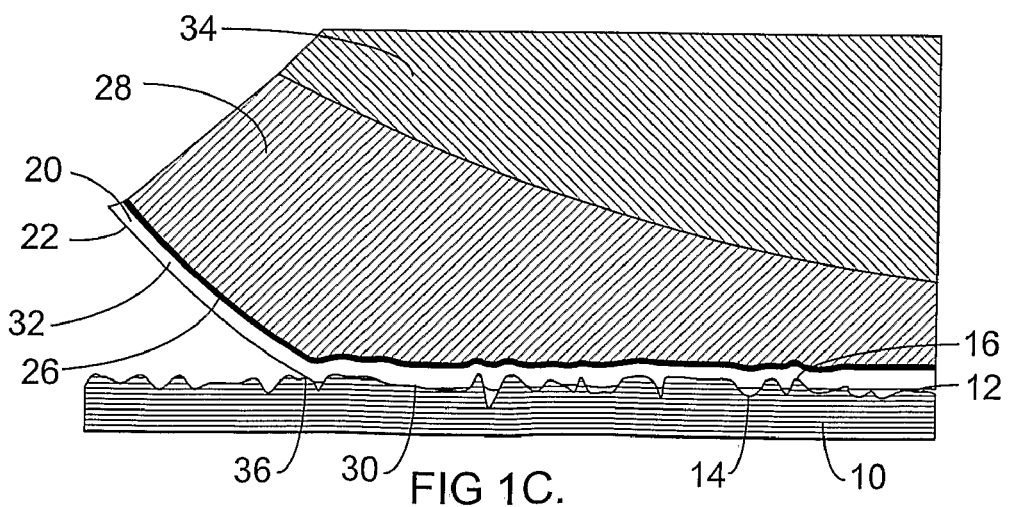
FIG. 1C is a sectional view illustrating a method of removing the viscoelastic probe surface from the test surface.

FIGS. 1A through 1C are sectional views illustrating the principle of utilizing the adhesion of a viscoelastic material to a rough surface to measure the surface energy of that surface. A solid 10 has a surface-under-test 12 which has some degree of roughness. There are many ways to characterize roughness; without precluding any particular characterization method of surface roughness, we will refer to a rough surface as having asperities 16 where the surface 12 protrudes above the average local surface of the solid 10, and pits 14 where the surface 12 lies below the average local surface of the solid. As the probe surface 22 approaches the test surface 12, the asperities 16 will make first contact.

The viscoelastic material (VEM) 20 is selected for both its chemical and mechanical properties. Preferred embodiments include silicones, rubbers, urethanes, acrylics, styrenes, and polyolifins. A most preferred embodiment is X4 retention gel from Gel-Pak of Hayward, Calif. An alternative most preferred embodiment is the adhesive component of 1310 removable clean room tape from UltraTape Industries of Oregon. The surface 22 of the VEM 20 can have the same composition as the bulk, or in a less preferred embodiment it can be treated with an adhesion promoter or inhibitor. The VEM 20 should leave minimal or no residue on the test surface 12 when it is removed, so that adhesion of the interface is tested and not cohesion of the VEM 20. The VEM thickness should be at least as great as the local roughness of the test surface; a useful range of VEM thickness is 0.0005 inches to 0.05 inches, with a most preferred thickness of about 0.005 inches.

A flexible support film 26 of relatively high modulus is useful in removing the VEM 20 from the test surface 12 without permanent stretching distortion. The most preferred support film is 0.002 inch thick Kapton. Kapton films down to 0.0002 inches can be used; the thinner films can experience stresses above their yield stress for high surface energy test surfaces. Kapton films up to 0.01 inches thick can be used; the thicker films can be sufficiently inflexible that don't conform to the larger lateral scale height variations of the test surface 12. Alternative preferred flexible support film materials include cellulose, polyesters, metal films, polyamides, and polyethylenes. One combination of the VEM 20 and the flexible support 26 is subsequently referred to herein as the ribbon.

A compressible layer 28 between the support film 26 and the mandrel 34 tends to make uniform the compression force pressing the VEM 20 against the test surface 12 particularly for length scales of roughness and curvature that are larger than the thickness of the VEM. The most preferred embodiment uses a 0.15 inch thickness of Poron polyurethane open cell foam with a 25% deflection of 1 to 5 psi. Poron is particularly useful in that it recovers quickly to its original configuration after a strain cycle. A preferred embodiment has a range of compressible layer thicknesses from 0.02 inches to 2 inches. Alternative compressible layer materials include open and closed cell foams, rubber, and elastomers.

A cylindrical mandrel 34 forms the hub of the probe in the most preferred embodiment. An alternative preferred embodiment is made by coating an o-ring or elastomeric torus with a VEM coating. Alternative embodiments of the mandrel 34 give its downward face a flat or spherical configuration; these will be subsequently described.

In FIG. 1A the mandrel 34 is pressed towards the test surface 12 while rotating clockwise and moving from left to right parallel to the test surface 12. The VEM probe surface 22 comes into contact with the test surface 12 at a leading edge 24. The attractive interaction between the VEM surface 22 and the test surface 12 tends to advance the mandrel 34 and the leading edge 24 to the right with respect to the test surface 10. Just behind the leading edge the asperities will tend to be in intimate contact with the VEM surface 22, such as asperity 32, while the pits may not be in intimate contact, such as pit 30.

In FIG. 1B the mandrel 34 continues to press towards the test surface 12 while rotating clockwise and moving from left to right parallel to the test surface 10. The normal pressure from the hub reaches its maximum where the mandrel tangent is parallel to the test surface 12. The combination of dwell time of the mandrel 34 over an area of the test surface and the pressure between the mandrel 34 and the test surface 12 causes the VEM 20 to conform to at least a portion of the rough surface that did not make contact near the leading edge. For example, the pit 30 generally makes intimate contact with VEM surface 22 in FIG. 1B.

In FIG. 1C the mandrel 34 continues to press towards the test surface 12 while rotating clockwise and moving from left to right parallel to the test surface 12. At the trailing edge 36 the VEM is peeling off of the test surface 12 by the rolling of the mandrel 34. The attractive interaction between the VEM surface 22 and the test surface 12 tends to retard the clockwise rotation of the hub as well as the linear motion of the mandrel 34 to the right with respect to the test surface 12. The mechanical dissipation in the VEM 20 that amplifies the surface energy as previously discussed occurs in the vicinity of the trailing edge 36.

The torque required to rotate the mandrel 34 in FIGS. 1A through 1C gives an averaged measurement of the difference between the forces retarding the trailing edge 36 and advancing the leading edge 24 combined with geometric effects such as the radius of the hub. In other geometries, such as the spherical ball described subsequently, the line of contact is a ring, and an external measure is the normal force required to remove the ball from the surface. We will subsequently refer to "drive force" to include both torque measurements on a mandrel and normal force measurements on a sphere. More generally, drive force is meant to be an external measurement of force acting in part on a line of contact between the test surface and the VEM.

Figure 2A:
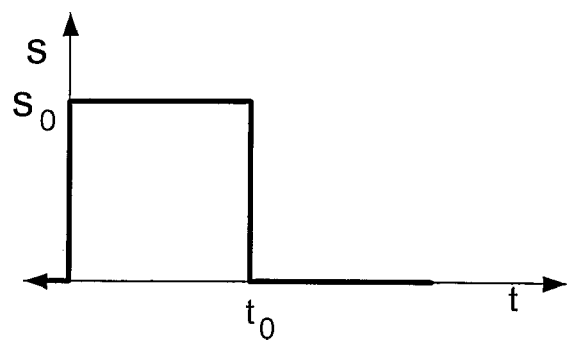
FIGS. 2A and 2B are graphs illustrating viscoelastic creep from a constant applied stress.
Figure 2B:
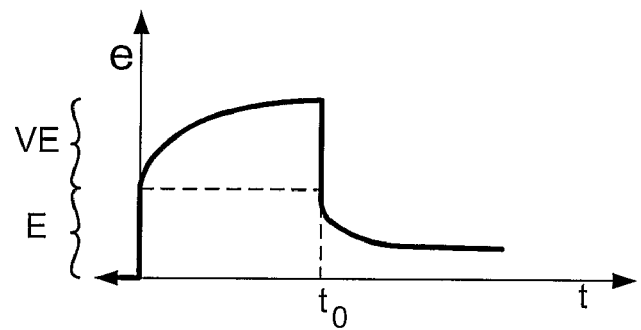

FIGS. 2A, 2B, 3A and 3B are graphs illustrating well known properties of viscoelastic materials. FIG. 2A shows a constant stress $\sigma_0$ being applied for a time $t_0$. FIG. 2B shows the strain $\epsilon$ that results from that applied stress. If the material were purely elastic, the strain would follow the dashed curve, promptly deflecting to the elastic strain limit E, and then fully recovering after $t_0$. A typical VEM follows the solid curve in FIG. 2B. The VEM also deflects initially to an elastic limit E, and then continues to experience additional strain as the VEM creeps. After $t_0$ the VEM will promptly partially recover, and then more gradually recover further. The time constants associated with creep and recovery, the relative magnitude of the elastic and viscoelastic strains, and the asymptotic recovery are idiosyncratically dependent on details of the material, the stress, and the geometry.

Figure 3A:
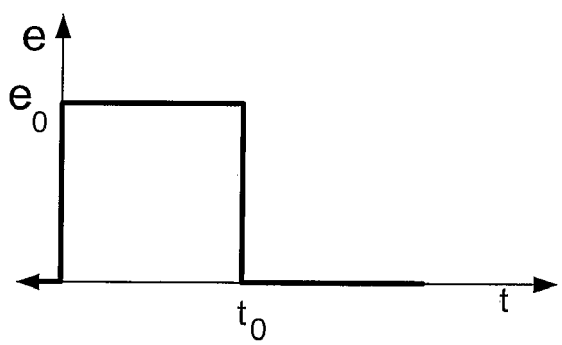
FIGS. 3A and 3B are graphs illustrating viscoelastic relaxation from a constant applied strain.
Figure 3B:
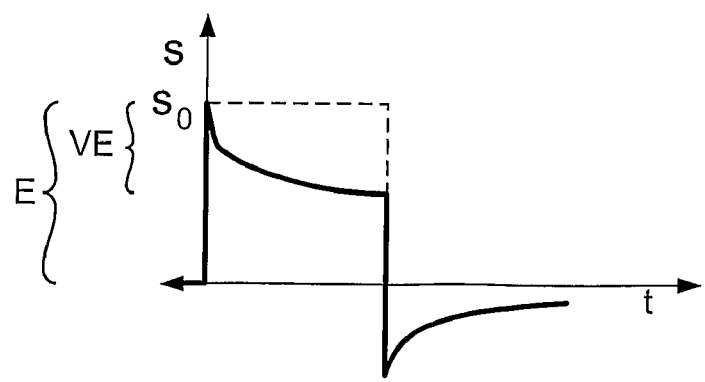

FIG. 3A shows a constant strain $\epsilon_0$ being applied for a time $t_0$. FIG. 3B shows the stress $\sigma$ that results from the applied strain. If the material were purely elastic, the stress would follow the dashed curve, promptly deflecting to the elastic stress limit E, and then fully recovering after $t_0$. A typical VEM follows the solid curve in FIG. 3B. The VEM also deflects initially to an elastic limit E, and then relaxes by VE to an intermediate stress level. After $t_0$ the VEM will experience some residual negative stress, which too will gradually relax. The time constants associated with relaxation, the relative magnitude of the elastic and viscoelastic strains, and the asymptotic recovery are again idiosyncratically dependent on details of the material, the stress, and the geometry.

Both creep and relaxation are experienced by the VEM 20 in FIG. 1A through 1C. For clarity, and without implied restrictions, we will subsequent refer to any combination of creep and relaxation as stress relaxation.

Figure 4A:
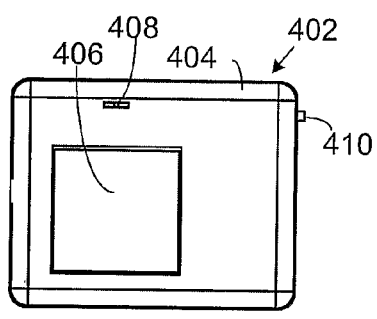
FIG. 4A is a top view of a portable, battery operated meter.
Figure 4B:
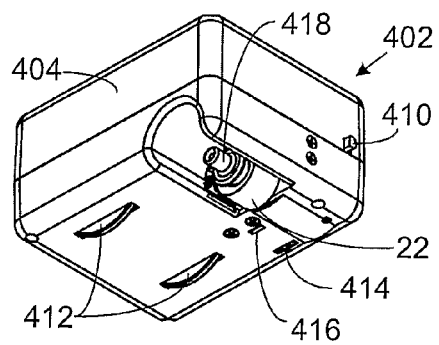
FIG. 4B is a bottom perspective view of the portable, battery operated meter.
Figure 4C:
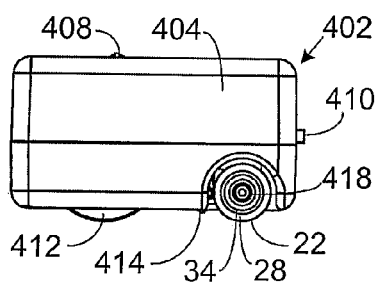
FIG. 4C is a side view of the portable, battery operated meter.
Figure 4D:
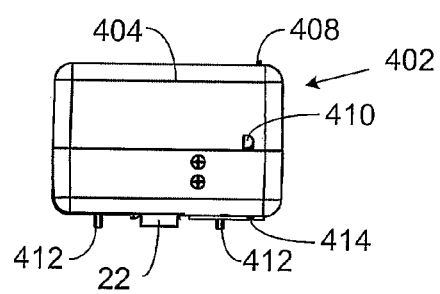
FIG. 4D is a front view of the portable, battery operated meter.
Figure 5A:
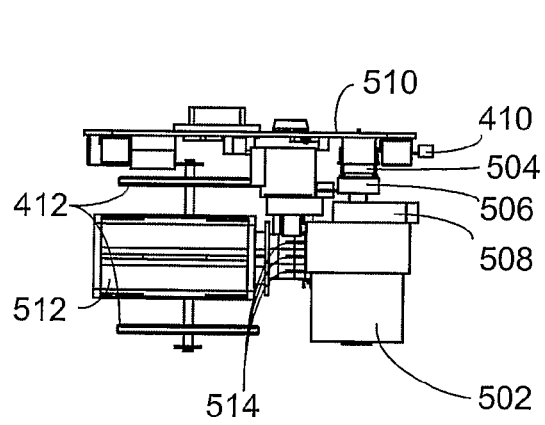
FIG. 5A is a top view of the portable, battery operated meter, where the case, touch screen display, and fasteners are omitted.
Figure 5B:
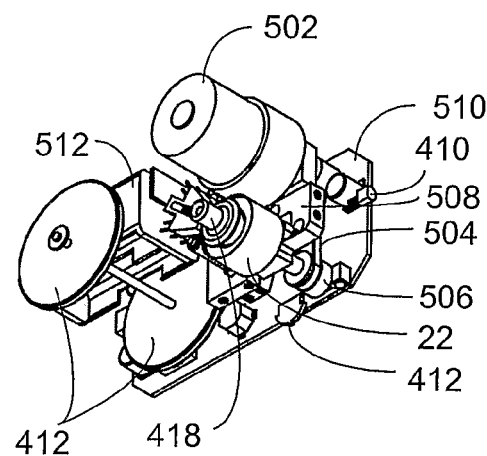
FIG. 5B is a bottom perspective view of the portable, battery operated meter, where the case, touch screen display, and fasteners are omitted.
Figure 5C:
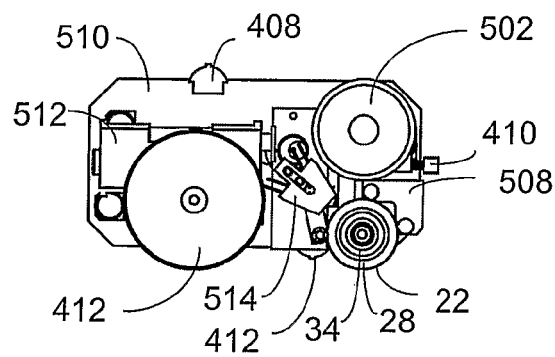
FIG. 5C is a side view of the portable, battery operated meter, where the case, touch screen display, and fasteners are omitted.
Figure 5D:
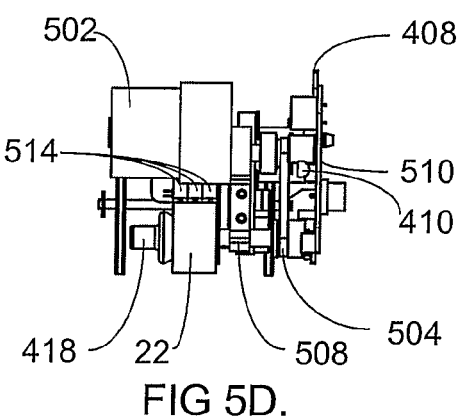
FIG. 5D is a front view of the portable, battery operated meter, where the case, touch screen display, and fasteners are omitted.

FIGS. 4A through 4D show four external views of portable, battery operated meter 402, which is a preferred embodiment of the invention. FIG. 4A is a top view of meter 402; FIG. 4B is bottom perspective view of meter 402; FIG. 4C is a left side view of meter 402; and FIG. 4D is a front view of meter 402. As shown, portable, battery operated meter 402 is roughly a three inch cube. The cuboid case 404 of injection molded plastic rests on top of a test surface 12 on two freely rotating wheels 412 and a portion of the surface 22 of a VEM 20. A touch screen display 406 provides visual readout of the surface energy of the test surface 12 upon completion of the measurement, as well as diagnostics, operation directions, and prompts. The touch screen and switches 408 and 414 give the user control of the functioning of the device. Since the apparent surface energy measured by the preferred embodiment is sensitive to temperature, the user can contact a temperature probe 410 to the test surface 12 to normalize the result to a standard temperature. A knob 418 aids in loading and removing ribbons from the assembly of an expandable mandrel 34 and the compressible layer 28. When the mandrel 34 is in its unexpanded state, the user slides a ribbon over the compressible layer 28, grasps the knob 418, and activates the switch 414. The meter 402 rotates the mandrel 34 by a mechanism described later, expanding the mandrel 34, and engaging the ribbon with the cylindrical surface of the compressible layer 28. A reflective optical sensor 416 determines if the unit is resting on a test surface or if it is in some other configuration.

FIGS. 5A through 5D are, respectively, a top view, bottom perspective view, left side view, and front view of the meter 402 (corresponding to FIGS. 4A through 4D, respectively), except that the case 404, the touch screen display 406, and various fasteners have been removed for clarity. A DC gear motor 502 drives pulleys 506 using belt 504 to controllably rotate the mandrel 34. The DC gear motor 502 and mandrel 34 are both mounted to a flexure bulkhead 508, describe later. A battery pack 512 provides power to a controller mounted on the printed circuit board 510. Three reflective optical sensors 514 are positioned to detect indicia on the ribbon, described later.

FIGS. 6A and 6B are front and side views, respectively, of the flexure bulkhead 508. The flexure bulkhead 508 mounts to the case 402 with the threaded holes 610. The DC motor 502 mounts through the hole 602, and the mandrel 34 mounts through the hole 604. Two slots 608 and four holes 612 are machined into the flexure bulkhead 508 so that the combination of the motor 502 and mandrel 34 are connected to the threaded holes via four thin flexures. Resistive film strain gages are glued to two of the four thin flexures at 606. Monitoring the differential resistance of the two strain gages provides the controller a measurement of the torque on the mandrel 34 with respect to the test surface 12.

FIGS. 7A through 7D are, respectively, a top view, bottom perspective view, left side view, and front view of the meter 402 (corresponding to FIGS. 4A through 4D, respectively), except that most of the constituent parts have been removed so that the self calibration mechanism can be more clearly seen. A bracket 702, held by threaded holds 712 to the case 402, carries a small stepper motor 704 and a pivot arm 706. An eccentric wheel 708 displaces the top end of the pivot arm 706 towards and away from the motor shaft, causing a calibration cylinder 710 to be alternately pressed against the VEM surface 22 or lifted off of the VEM surface 22. A spring 712 preloads the pivot arm 706 against the eccentric wheel 708. The calibration cylinder serves several functions. Since its surface energy is known, measuring its surface energy by rolling the calibration cylinder 710 in contact with a known good VEM 22 and measuring the resulting torque allows the strain gages to be calibrated. The more common function of the calibration cylinder is to test the VEM surface 22 to see if a previous test surface 12 has contaminated the VEM, which would reduce the apparent surface energy of the calibration cylinder.

Figure 8:
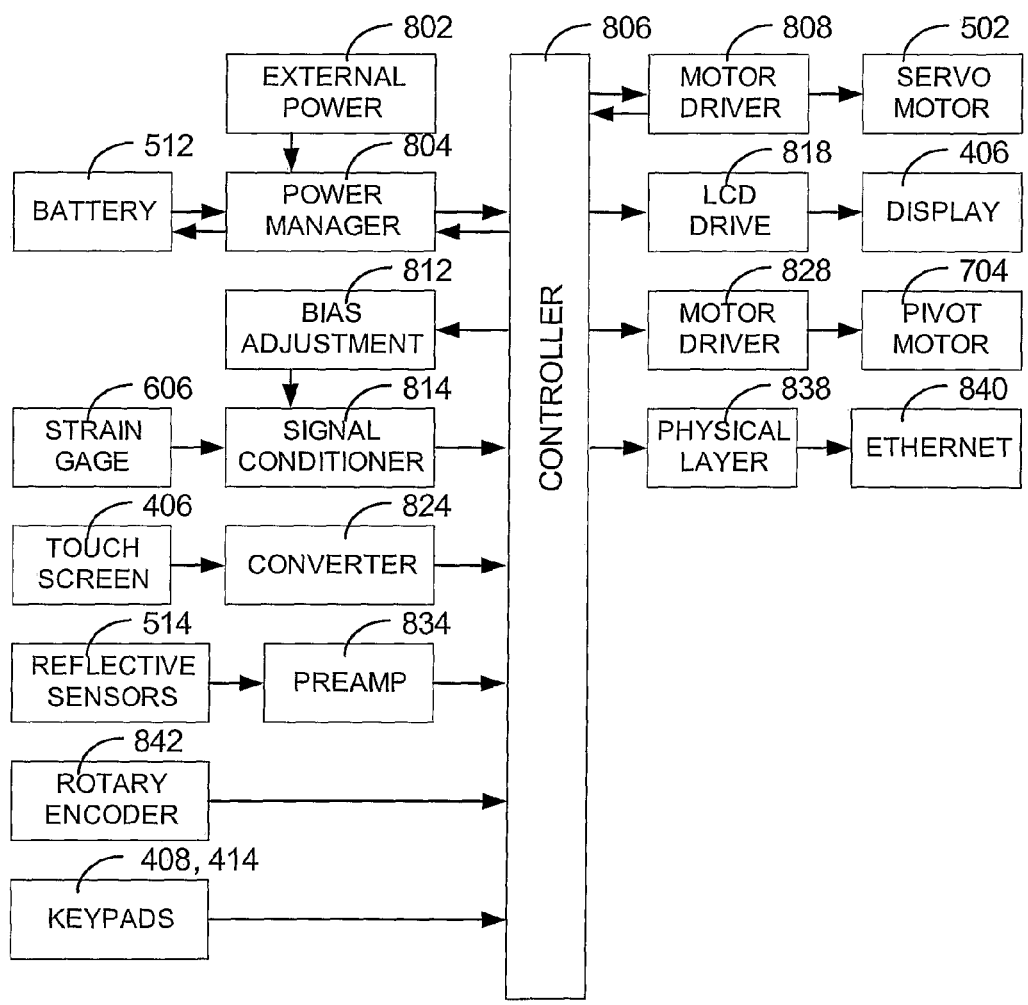
FIG. 8 is a block diagram illustrating the control system of a preferred embodiment of the invention.

FIG. 8 is a block diagram illustrating the signal connections of a preferred embodiment of the meter 402. A rechargeable battery 512 supplies power to the system through a power manager 804. The power manager can be as simple as a switch; in the most preferred embodiment the power manager is a circuit executing the functions of gas gage, charging control, temperature and short circuit protection, and multi-level power conservation. A connector to an external charging device 802 allows the power manager 804 to recharge the battery 512. A controller 806, consisting of one or more processors and their associated memory and programming, coordinates the operation of the peripheral devices and performs calculations related to test surface energy. An example of a controller is a dsPIC30F6014A. Variations in the resistance of the strain gages 606 are converted to a signal by a signal conditioner 814. Since test surfaces with low surface energies may generate only small torques, a DAC 812 is used to null the bias to the signal conditioner 814. The four wire output from the touch screen 406 is processed by a converter 824, which in turn sends interrupts and x-y screen coordinates to the controller 806. Reflective sensors 514 measure both indicia on the ribbon and the presence of a test surface; signals from the reflective sensors 514 pass through a preamplifier 834 to the controller 806. A rotary encoder 842 monitors the angular position of the mandrel. The motor driver 808 converts servo motor signals from the controller 806 into higher power drive signals to the servo motor 502 that rotates the mandrel. A second motor driver 828 allows the controller 806 to position the stepper pivot motor 704 for auto-calibration or normal operation. The controller 806 writes to the LCD display 406 through an LCD drive controller 818. In addition to displaying results on the LCD, an external data interface is available through an Ethernet port 840 connected to the controller 806 through a physical layer interface 838.

Figure 9:
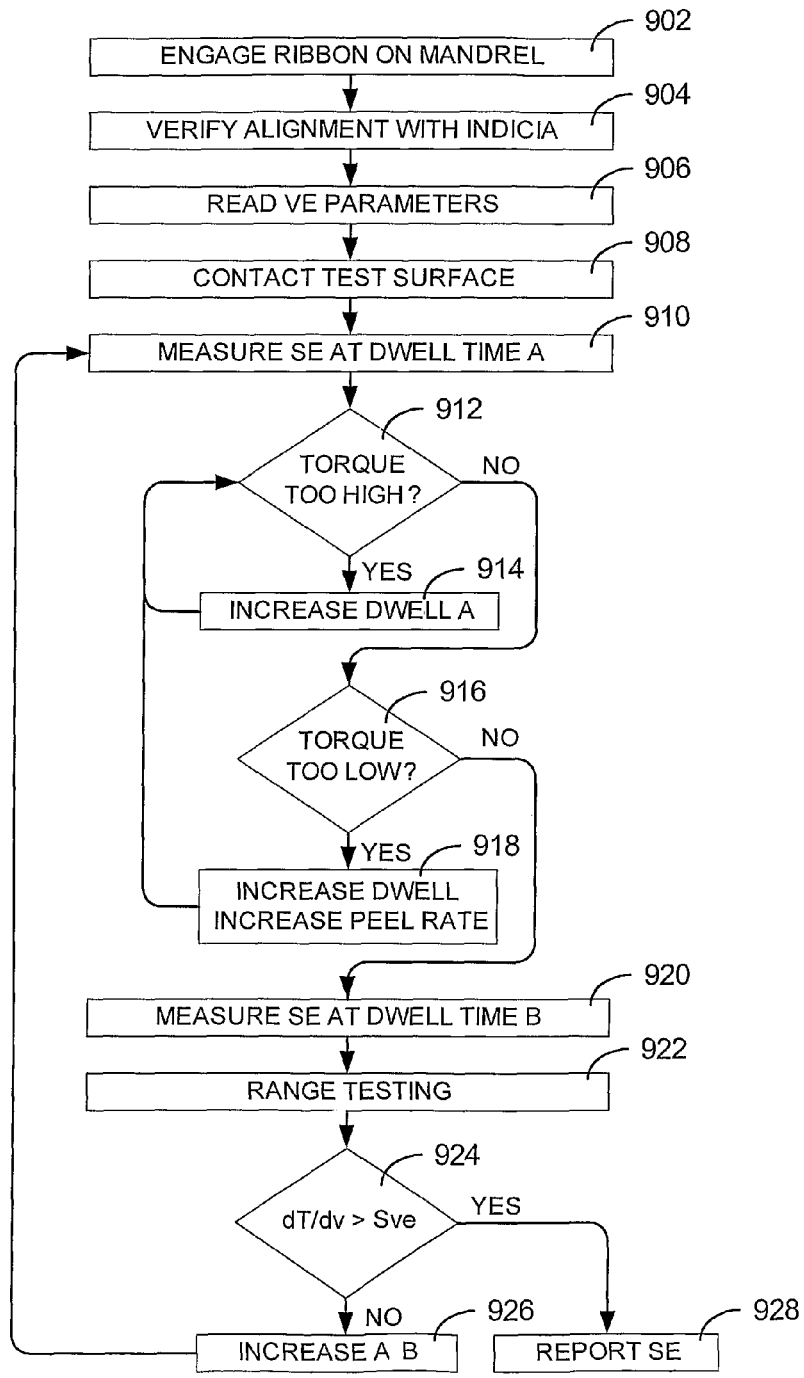
FIG. 9 is a process flow chart illustrating the decision flow of a measurement process of a preferred embodiment of the invention.

FIG. 9 is a process flow chart for a preferred embodiment of the meter 402. Starting with a ribbon-free mandrel 34, the user slides a ribbon over the foam sleeve of the mandrel and operates the knob 418 and switch 412 to expand the mandrel 34 and engage the ribbon 902. The controller 806 inputs reflective sensor readings while causing the mandrel 34 to rotate, reading indicia on the ribbon. The indicia are tested for alignment errors 904 like a missing ribbon or a ribbon positioned incorrectly along the axis of the mandrel. If the indicia indicate a valid ribbon is located correctly, viscoelastic parameters 906 are extracted from the indicia. The user places the preferred embodiment 402 with the ribbon surface in contact with the test surface 908, and the user indicates that the measurement should start.

To measure the surface energy (SE), the controller causes the mandrel 34 to rotate at a predetermine rate. The dwell time is the time the trailing contact edge 36 intersects a point on the ribbon minus the time the leading contact edge 24 intersects that point on the ribbon. The dwell time is related to the ribbon circumference, the preload, the rotation rate, and the mandrel 34 diameter. When at least half of one dwell time has passed, so that the rolling process has approached steady state, the controller reads the torque required to rotate the mandrel using the strain gage signals. The controller can average several such measurements to improve signal to noise, or can accumulate a sequence of such measurements to create a spatial map. The controller then reverses the direction of rotation of the mandrel 34, again allows steady state to be reached, and acquires torque data while moving in the reverse direction. The difference between the torque readings in the plus and minus directions makes the measurement process less sensitive to offsets in the sensors; it also compensates for the test surface being out of level. Finally the torque readings are combined with the viscoelastic parameters using a predetermined function to produce the measured surface energy (SE).

The torque is tested to see if it is too high 912. For example, if the surface adheres sufficiently to the ribbon, the torque required to rotate the mandrel will lift the wheels 412 completely off of the test surface if the mandrel rotation direction is reversed; in this case, the reverse direction reading is generally not required to improve signal to noise, and only the forward direction is used. If the torque is so high that the strain gage measurement leaves its calibrated range 914, then the peel rate should be decreased by increasing the dwell time, and the measurement 910 repeated. If the torque is so low that there is little detectable difference between the forward and reverse torques 918, again the dwell time should be increased to test for the case that the VEM has not undergone enough stress relaxation to compensate for the surface roughness, and the measurement 910 repeated.

If the SE measurement at dwell time A has passed the range tests 912 and 916, a second SE measurement is then made at dwell time B 920, different from dwell time A. Again, range tests 922 are applied. The two surface energy measurements SE(A) and SE(B) are used to compute a rate of change of torque with peel velocity 924; if this slope is greater than a value computed from the viscoelastic parameters, a well adhered and sufficiently stress relaxed interface is indicated, and the final surface energy is reported 928. If the slope is less than a value computed from the viscoelastic parameters 926 the dwell times are increased and the measurement cycle is repeated.

Since quicker measurements have more value than slower measurements, the first measurement dwell time A tried should be somewhat smaller than the dwell time A used in the last successful measurement cycle. This is done so that repeated measurements performed in a manufacturing application cause the measurement cycle to equilibrate near the shortest practical time.

The process illustrated in FIG. 9 assumes that measurements are made in steady state, or with the mandrel 34 rotating at a constant speed. An alternative preferred embodiment for relatively rough low surface energy test surfaces uses a stop-and-go approach. The ribbon is compressed against the test surface by a stationary mandrel 34 for a dwell time, then the mandrel 34 is rotated at a relatively high rate to peel off the ribbon adhered during the dwell time. Since the ribbon contacting the test surface 12 during the dwell time experiences a non-uniform compression, the SE should be computed from the torques measured as the ribbon under the center of the stationary mandrel 34 is peeled off the test surface 12.

The moving leading and trailing contacts propelled by the rolling mandrel 34 reach steady state values in a fraction of a full rotation of the mandrel 34. This allows the preferred embodiment to consider a ribbon as several independent sectors. A sector need be no larger than about two static footprints of the ribbon contacting the test surface 12. The number of sectors per ribbon is between two and thirty two, with six sectors being the most preferred value. When a new ribbon is engaged on the mandrel 34, each sector can be treated as a fresh probe surface uncontaminated by previous measurements.

Figure 10:
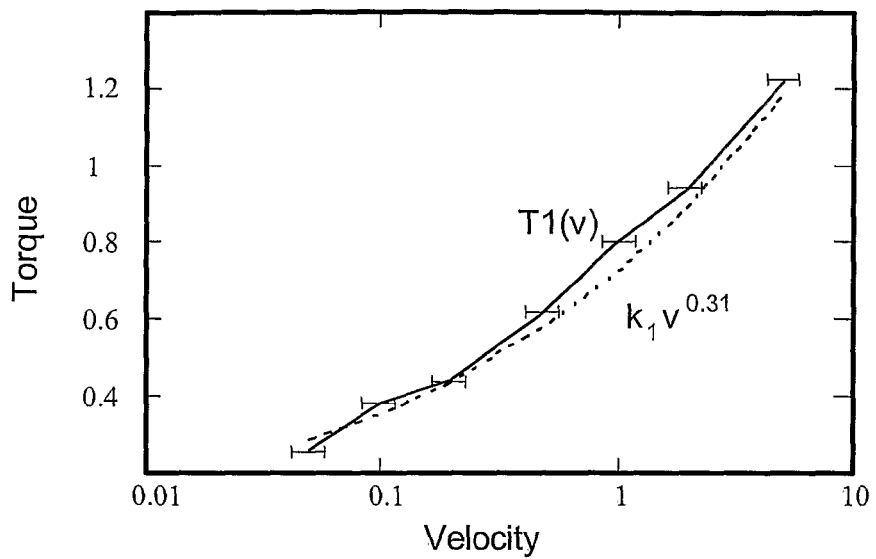
FIG. 10 is a graph illustrating data measuring the surface energy of a smooth surface by a preferred embodiment of the invention.

FIG. 10 is a graph showing experimental data taken from a ribbon rolling across a clean native oxide silicon wafer. A linear torque scale is plotted against a logarithmic leading edge velocity scale. Over about two orders of magnitude of velocity, this particular removable pressure sensitive adhesive shows a reasonable fit to a 0.31 power law dependence on velocity, shown by the dashed curve.

Figure 11:
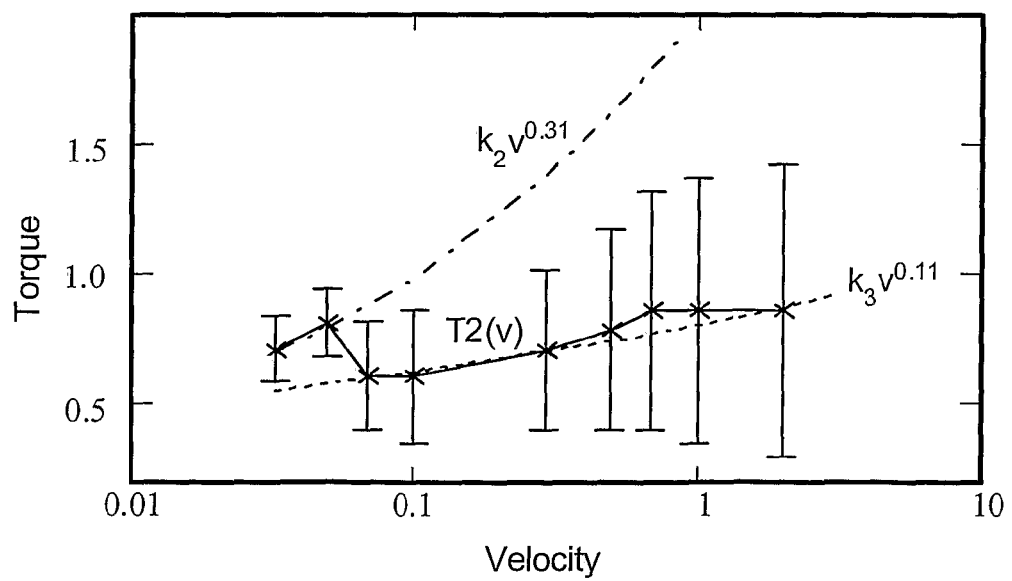
FIG. 11 is a graph illustrating data measuring the surface energy of a rough surface by a preferred embodiment of the invention.

FIG. 11 is a graph showing experimental data for the same pressure sensitive adhesive rolling across a clean flat steel plate to which 40 μm diamonds have been adhered (a diamond lap tool). At low rolling velocities, the required torque appears to follow a similar power law to the smooth surface data of FIG. 10. At higher rolling velocities, the required torque changes less rapidly with velocity, following approximately a 0.11 power law. We note that there can be an audible distinction between the low and high velocity cases; the low velocity case is relatively silent, while the high velocity case can produce a crackling sound.

Figure 12:
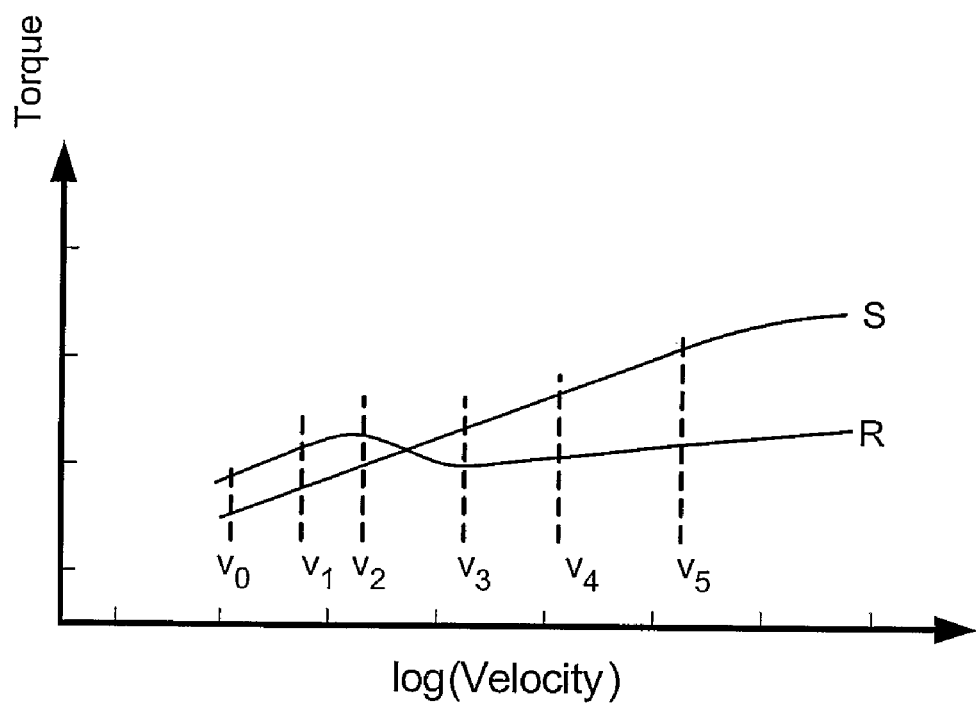
FIG. 12 is a graph illustrating characteristics of data measuring the surface energy of smooth and rough surfaces by a preferred embodiment of the invention.

FIG. 12 is a graph illustrating a generic comparison between rolling torques measured on relatively smooth (S) and relatively rough (R) test surfaces of the same chemical composition. At the lowest velocities ($v<v_1$), the VEM is in intimate contact with both S and R; since there is more area in contact and some mechanical interlocking between the test surface and the VEM in the R case, there is more torque required for the rough surface. As the velocity increase ($v_1<v<v_3$), the stress relaxation reduces in the R case from forming good contact with the asperities and the pits to forming good contact with just the asperities. In this range the torque is somewhat unpredictable; experimentally the required torque can appear oscillatory. At still higher velocities ($v_3<v_5$) the rough surface is producing less torque and is following a different power law compared to the smooth surface. The smooth surface ceases to follow its low velocity power law above $v_5$.

Figure 13:
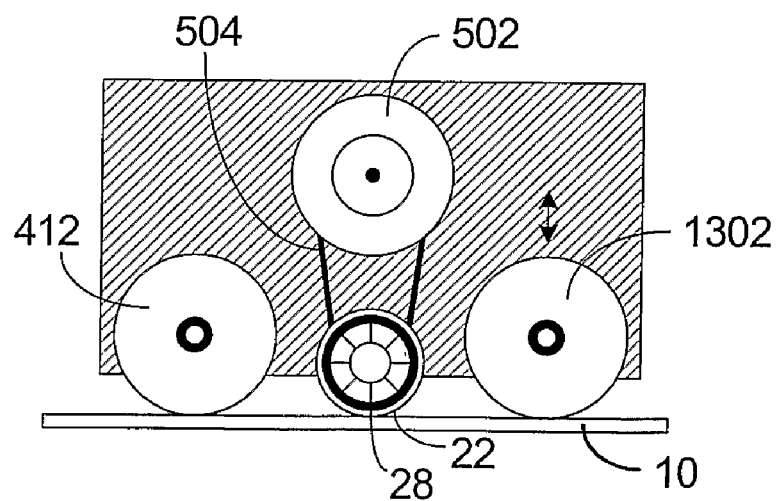
FIG. 13 is a side view illustrating an alternative preferred embodiment of the invention.

FIG. 13 is a side view illustrating an alternative preferred embodiment meter, where the leading and trailing edges move in opposite directions instead of the same direction. An additional wheel 1302 is added that is controlled by a motor to move vertically, thereby pressing the probe surface 22 against the test surface or separating the probe surface from the test surface. In this case, the force exerted by the test surface on mandrel normal to the test surface is measured as a function of the height of the additional wheel 1302, giving a measurement of the surface energy in the contacting area under the mandrel. The rotating mandrel is useful to move the sensing unit laterally, as well as for advancing the probe surface to a clean, un-used position for the next test sample. In alternative preferred embodiments the probe surface that contacts the test surface is toroidal, flat, or cylindrical prior to contacting the test surface.

The preferred embodiment meter shown in FIG. 13 can be used to measure surface energy with constant velocity but varying preload. In this application, the wheels 412 and 1302 support a portion of the weight of the measurement tool, and the mandrel supports the remaining weight. The fraction of the weight of the measurement tool supported by the mandrel is varied by adjusting the vertical position of wheel 1302. Increasing the stress forcing the VEM into a rough test surface will increase the number of pits in intimate contact with the probe surface for a constant dwell time.

Figure 14:
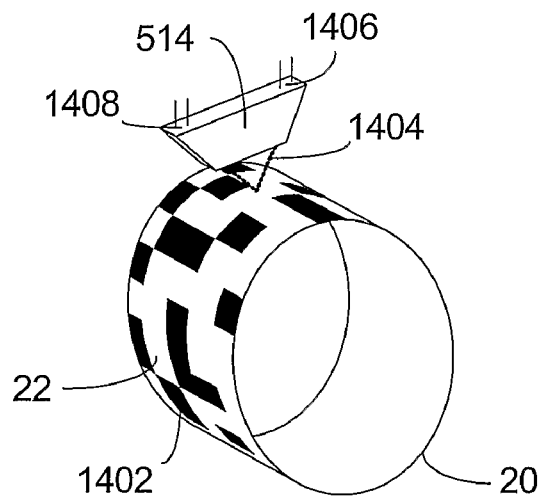
FIG. 14 is a perspective view illustrating measuring indicia associated with the probe surface of a preferred embodiment of the invention.

FIG. 14 is a perspective view illustrating a preferred embodiment of the ribbon with optically detectable indicia. As the mandrel rotates the ribbon, a circumferential band of the ribbon passes under a reflective optical sensor 514. A light source 1406 in the reflective sensor 514 produces a light beam 1404 that reflects off of the probe surface 22 and onto a light sensor 1408. The signal from the light sensor 1408 can measure the presence or absence of indicia on the surface, including gray scale values. Several sensors at different axial position will measure indicia in different circumferential bands. These indicia can be coded with alignment marks, serial numbers, sector identifiers, and viscoelastic parameters for the VEM used in the ribbon.

Figure 15A:
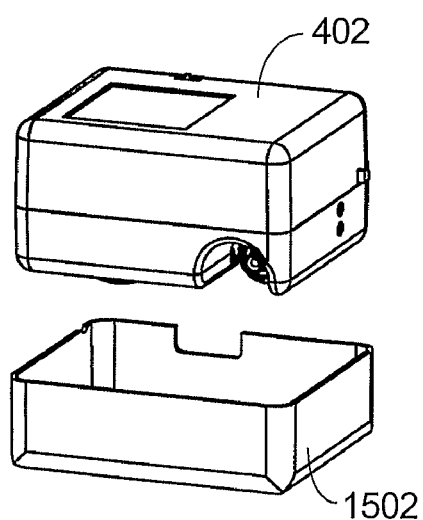
FIGS. 15A and 15B are perspective views illustrating a preferred embodiment of the invention separated from a storage tray and assembled with a storage tray, respectively.
Figure 15B:
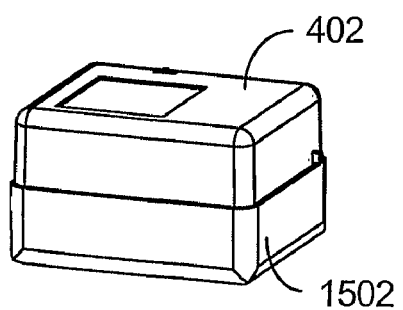

FIGS. 15A and 15B are perspective views illustrating the use of a tray 1502 with the preferred embodiment meter 402. In FIG. 15A the meter 402 is separate from the tray 1502; in FIG. 15B the meter 402 is nested into the tray 1502. The tray can serve to protect a mounted ribbon from contamination when the meter is not in use. The tray can support the meter so that the mandrel is free to rotate; this is useful during auto calibration with the calibration cylinder 710.

In an alternative preferred embodiment, the thickness of the VEM 20 is varied on the flexible support film 26. A readily implemented version of this embodiment has the VEM thickness varying linearly about the circumference of the ribbon. Since the VEM looses its ability to conform to the surface roughness once the VEM thickness is less than the surface thickness, this is a method provides quantitative surface roughness information in addition to surface energy.

FIGS. 16A through 16F illustrate aspects of a compact configuration of the invention. FIG. 16A is a side view of the complete apparatus. FIG. 16B is a sectional view of section A-A taken in FIG. 16A. FIG. 16C is a perspective view of the complete apparatus with the standoff 1608 separated. FIG. 16D is a side view of the disposable applicator assembly 1604. FIG. 16E is a sectional view of section B-B taken in FIG. 16D. FIG. 16F is also a sectional view of section B-B taken in FIG. 16D, which illustrates the distortion of the disposable application 1604 when pressed against a test surface 12.

FIG. 16A is a preferred embodiment in which the probe surface 22 is initially spherical, and the actions of stressing, relax, and delaminating the interface between the probe surface 22 and the test surface 12 involves motions in a line normal to the surface. An advantage to this configuration is compactness; the AA battery 1618 and linear stepper motor 1616 are to scale for a 6 inch long 0.87" diameter pen-style design. Externally the user would hold the plastic case 1606 while pressing the removable standoff 1608 against the test surface 12.

FIG. 16B shows cross sections of components of FIG. 16A. Probe surfaces are stored in a cylindrical stack of disposable applicator assemblies 1604 held within a ferromagnetic guide tube 1610. The guide tube 1610 holds the disposable applicator assemblies 1604 in a snug sliding fit. A magnet 1612 binds the end of the guide tube 1610 to a sensitive force gage 1614 that generates signals proportional to axial compression or tension. The force gage is mounted in turn on the non-rotating shaft of a linear stepper motor 1616 such as a Haydon Linear 2000. A battery 1618 provides power to a controller (not shown). To expose a fresh probe surface, the user first slides the guide tube 1610 axially away from the magnet 1612 and out of the case 1606. In a manner analogous to U.S. Pat. No. 3,338,215, the user loosens the previously exposed disposable applicator assembly 1604 from the tapered end of the guide tube 1610, and then inserts that used applicator assembly 1604 in the end of the guide tube 1610 usually contacting the magnet 1612 such that the previously exposed disposable applicator mates with the disposable applicators still in the guide tube, pushing them through the tube till a newly exposed disposable applicator emerges from the tapered end of the guide tube. Then the user slides the guide tube 1610 with its re-ordered disposable applicator assemblies 1604 back into the case 1606 and in contact with the magnet 1612.

FIG. 16D shows a side view of a disposable applicator assembly 1604, consisting of a molded cartridge 1620 and a viscoelastic sphere 1622. When a user initiates a measurement cycle, the standoff 1608 is in place on the end of the case 1604, and the free end of the standoff is pressed against the test surface 12. The linear stepper motor 1616 provides sufficient force to drive the exposed disposable applicator assembly 1604 towards the test surface until the shoulder of the molded cartridge 1620 contacts the test surface 12. After a sufficient time for stress relaxation, the linear stepper motor 1616 retracts the combination of the force gage 1614, the magnet 1612, the guide tube 1610, and the cylindrical stack of disposable applicator assemblies 1604 from the test surface which measuring the force or tension required. The surface energy of the test surface is then computed by the controller.

Although the present invention has been described with reference to preferred embodiments, workers skilled in the art will recognize that changes may be made in form and detail without departing from the spirit and scope of the invention.

The invention claimed is:

1. An apparatus for measuring a surface energy of a test surface having a plurality of asperities and pits, the apparatus comprising:
   a moveable component having a surface;
   a viscoelastic polymer layer disposed on the surface of the moveable component, and configured to engage the test surface under an applied compressive force;
   a motor configured to move the moveable component along the test surface;
   a controller in signal communication with the motor, the controller being configured to direct the motor to move the moveable component at a predetermined velocity along the test surface, wherein the controller monitors a drive force applied to the moveable component while moving; and
   a control algorithm operated by the controller, and configured to determine the surface energy of the test surface based at least in part on the compressive force applied to the viscoelastic polymer layer, the predetermined velocity, and the monitored drive force.

2. The apparatus of claim 1, wherein the moveable component is rotatable, and wherein the predetermined velocity is a predetermined rotational velocity.

3. The apparatus of claim 1, wherein the determined surface energy of the test surface is further based on at least one surface energy parameter of the viscoelastic polymer layer.

4. The apparatus of claim 3, wherein the determined surface energy of the test surface satisfies a first criteria that a stress applied to the viscoelastic polymer layer adjacent a portion of the asperities is relaxed.

5. The apparatus of claim 4, wherein the determined surface energy of the test surface satisfies a second criteria that the viscoelastic polymer layer contacts a portion of the pits.

6. The apparatus of claim 1, wherein the controller is configured to move the moveable component at a plurality of predetermined velocities, and wherein the control algorithm is configured to determine surface energies of the test surface for each of the plurality of predetermined velocities.

7. The apparatus of claim 1, wherein the moveable component is selected from the group consisting of a cylindrical component, a spherical component, and a torus component.

8. The apparatus of claim 1, wherein the surface of the moveable component is a circumferential surface that is expandable for adjusting a diameter of the moveable component.

9. The apparatus of claim 1, further comprising a support tray.

10. An apparatus for measuring a surface energy of a test surface having a plurality of asperities and pits, the apparatus comprising:
    a cylindrical component having a circumferential surface and a viscoelastic polymer layer disposed on the circumferential surface, the cylindrical component being positionable relative to the test surface such that the viscoelastic polymer layer contacts the test surface under an applied compressive force;
    a motor configured to rotate the cylindrical component at a predetermined rotational velocity along the test surface;
    a torque sensor configured to monitor torque required to rotate the cylindrical component, and to relay torque signals based on the monitored torque;
    a controller in signal communication with the torque sensor for receiving the relayed torque signals; and
    a control algorithm operated by the controller and configured to determine the surface energy of the test surface based at least in part on the compressive force applied to the viscoelastic polymer layer, the predetermined rotational velocity, and the monitored torque.

11. The apparatus of claim 10, wherein the determined surface energy of the test surface is further based on at least one surface energy parameter of the viscoelastic polymer layer.

12. The apparatus of claim 10, wherein the controller is configured to rotate the rotatable component at a plurality of predetermined rotational velocities, and wherein the control algorithm is configured to determine surface energies of the test surface for each of the plurality of predetermined rotational velocities.

13. The apparatus of claim 10, wherein the rotatable component is selected from the group consisting of a cylindrical component, a spherical component, and a torus component.

14. The apparatus of claim 10, wherein the circumferential surface of the rotatable component is expandable for adjusting a diameter of the rotatable component.

15. A method of measuring a surface energy of a test surface having a plurality of asperities and pits, the method comprising:
    providing a moveable component having a surface and a viscoelastic polymer layer disposed on the surface;
    positioning the viscoelastic polymer layer in contact with the test surface;
    compressing the viscoelastic polymer layer between the test surface and the moveable component with a compressive force;
    moving the moveable component along the test surface in a first direction at a predetermined velocity;
    measuring a first drive force applied to the moveable component while moving the moveable component along the test surface; and
    determining the surface energy of the test surface based at least in part on the compressive force, the predetermined velocity, and the measured first drive force.

16. The method of claim 15, further comprising:

moving the moveable component with respect to the test surface at a second predetermined velocity; and measuring a second drive force applied to the moveable component while moving the movable component at the second predetermined velocity, wherein the surface energy of the test surface is further based on the second predetermined velocity, and the measured second drive force.

17. The method of claim 15, wherein the viscoelastic polymer layer has multiple layer thicknesses.

18. The method of claim 15, wherein moving the moveable component comprises rotating the moveable component, wherein the first direction comprises a first rotational direction, and wherein the predetermined velocity is a predetermined rotational velocity.

19. The method of claim 18, further comprising:

rotating the moveable component along the test surface at the predetermined rotational velocity in a second rotational direction that is opposite of the first rotational direction; and measuring a second drive force applied to the moveable component while rotating the moveable component in the second rotational direction, wherein the surface energy of the test surface is further based on the measured second drive force.

20. The method of claim 18, further comprising:

placing the viscoelastic polymer layer on the surface of the moveable component, wherein the surface of the moveable component is a circumferential surface; and expanding the surface for increasing a diameter of the moveable component.

* * * * *